(12) United States Patent
Uemura

(10) Patent No.: US 11,260,243 B2
(45) Date of Patent: Mar. 1, 2022

(54) INFRARED SUDATION DEVICE

(71) Applicant: IYASHI DÔME, Paris (FR)

(72) Inventor: Shogoro Uemura, Carouge (CH)

(73) Assignee: Iyashi Dôme, Paris (FR)

( * ) Notice: Subject to any disclaimer, the term of this patent is extended or adjusted under 35 U.S.C. 154(b) by 781 days.

(21) Appl. No.: 16/063,964

(22) PCT Filed: Dec. 13, 2016

(86) PCT No.: PCT/FR2016/053354
§ 371 (c)(1),
(2) Date: Jun. 19, 2018

(87) PCT Pub. No.: WO2017/109332
PCT Pub. Date: Jun. 29, 2017

(65) Prior Publication Data
US 2018/0304096 A1    Oct. 25, 2018

(30) Foreign Application Priority Data

Dec. 22, 2015   (FR) ..................................... 1563065

(51) Int. Cl.
  *A61N 5/06*   (2006.01)
  *A61F 7/00*   (2006.01)
  *C03C 17/23*  (2006.01)

(52) U.S. Cl.
  CPC .............. *A61N 5/0625* (2013.01); *A61F 7/00* (2013.01); *C03C 17/23* (2013.01); *A61F 7/007* (2013.01);
(Continued)

(58) Field of Classification Search
CPC combination set(s) only.
See application file for complete search history.

(56) References Cited

U.S. PATENT DOCUMENTS 6,549,809 B2    4/2003   Ono

FOREIGN PATENT DOCUMENTS

| CN | 2774214 Y | 4/2006 |
| CN | 2794544 Y | 7/2006 |

(Continued)

OTHER PUBLICATIONS

International Search Report and Written Opinion for PCT/FR2016/053354, dated Mar. 7, 2017.
(Continued)

*Primary Examiner* — Joseph A Stoklosa
*Assistant Examiner* — Adam J Avigan
(74) *Attorney, Agent, or Firm* — Merchant & Gould P.C.

(57) ABSTRACT

An infrared sudation device includes a support element (1) extending along a longitudinal axis (X) and a cover element (2a, 2b) of semicylindrical shape mounted on the support element (1) so as to delimit an internal volume extending in the longitudinal direction between the support element and the internal surface of the cover element. The internal surface of the cover element is covered at least in part with a heating layer (3a, 3b) able to emit far-infrared radiation in at least part of the internal volume. The infrared sudation device includes a housing of photocatalyst (4), permeable to the infrared radiation emitted, supporting a photocatalyst (5) and arranged in proximity to the internal face of the heating layer (3a, 3b) so as to allow the photocatalyst to be activated using the energy supplied by the infrared radiation emitted.

10 Claims, 1 Drawing Sheet

(52) U.S. Cl.
CPC .......... *A61F 2007/0052* (2013.01); *A61F 2007/0088* (2013.01); *A61N 5/0616* (2013.01); *A61N 2005/066* (2013.01); *A61N 2005/0636* (2013.01); *A61N 2005/0637* (2013.01); *C03C 2217/71* (2013.01)

(56) References Cited

FOREIGN PATENT DOCUMENTS

| | | | |
|---|---|---|---|
| EP | 0980709 A1 | | 2/2000 |
| EP | 2072666 A1 | | 6/2009 |
| FR | 2931685 A1 | | 12/2009 |
| JP | 2008-011996 A | | 1/2008 |
| KR | 101169386 | * | 7/2012 |
| WO | 2015/059313 A1 | | 4/2015 |

OTHER PUBLICATIONS

PCT Third Party Observation for PCT/FR2016/053354, dated Apr. 20, 2018.
Webpage/spabusiness.com, "Cllinical trial confirms effectiveness of Iyashi Dome", http://www.spabusiness.com/detail.cfm?subID=260953&pagetype=detail&subject=product&codeID=311497&dom=y, retrieved Jun. 19, 2018.

* cited by examiner

INFRARED SUDATION DEVICE

This application is a National Stage Application of PCT/FR2016/053354, filed 13 Dec. 2016, which claims benefit of French Patent Application No. 1563065, filed 22 Dec. 2015, which applications are incorporated herein by reference. To the extent appropriate, a claim of priority is made to each of the above-disclosed applications.

BACKGROUND OF THE INVENTION

The invention generally relates to the field of devices for the treatment in particular of the skin via radiation and relates more particularly to an infrared sudation device and in particular via infrared of the long type.

SUMMARY OF THE INVENTION

The use of infrared waves in therapy, in particular waves of the far infrared type also called IR-C, or long infrared, the wavelength of which is between 3 μm and 1000 μm, allows for a resonance of the muscle tissue that increases certain cellular functions generating a sudation that is particularly effective for improving the quality of the skin and of its physiological properties. In particular, the radiant energy provided by an infrared radiation device in this range of wavelengths procures an in-depth detoxification of the upper layers of the human body, with a beneficial effect on well-being and on health. This is because, contrary to a conventional sauna where the heat is transmitted to the body by heating the ambient air, the infrared radiation device makes it possible to heat the body directly with the heat produced by the infrared radiation. The heat diffused by the long infrared thus penetrates deeply into the skin and makes it possible to effectively eliminate through sweat the excessive toxins, including toxic heavy metals to which the individuals may have been exposed, such as strontium, barium, nickel, lead, molybdenum, tellurium, chromium, cobalt, arsenic, cadmium, aluminium and copper. This is because these heavy metals are substantially excreted by sweat. Thus the exposure to long infrared radiation makes it possible to increase the elimination of heavy metals. It has been able to be observed through studies aimed at evaluating the effectiveness of a long-infrared radiation device that the physiological and biomechanical properties of the skin of an individual using such a device were improved (better skin density, better skin elasticity and firmness of the skin, attenuation of wrinkles, etc.).

Patent document U.S. Pat. No. 6,549,809 discloses a long-infrared radiation device of the type comprising a support intended to receive a user in lying position and an infrared emissions portion to irradiate the user, formed from two semi-cylindrical portions sliding over one another and able to cover the user lying on the support. The semi-cylindrical portions are provided along their internal surface with means of infrared emission comprising a heating layer with a black-carbon base fixed to the internal surface and able to provide a radiation in the desired wavelengths in the volume located between the support and the semi-cylindrical portions that cover it. However, repeated use of the device causes a saturation of the air with toxins eliminated through sweat, which is harmful and unhygienic.

In this context, the purpose of this invention is to propose a device free from the aforementioned limitation.

For this purpose, the invention relates to an infrared sudation device comprising a support element extending along a longitudinal axis intended to receive a user in lying position and a cover element of semi-cylindrical shape mounted on said support element so as to delimit an internal volume extending in the longitudinal direction of said support element between said support element and the internal surface of said cover element, said internal surface of said cover element being covered at least in part with a heating layer able to emit far-infrared radiation in at least one portion of said internal volume, said device being characterised in that it comprises a photocatalyst housing, permeable to the infrared radiation emitted, supporting a photocatalyst and being arranged in proximity to the internal face of said heating layer, so as to allow said photocatalyst to be activated using the energy supplied by said infrared radiation emitted.

Thanks to this arrangement, it is possible to decontaminate and clean up the air present in the internal volume subjected to infrared radiation during the unfolding of an irradiation session. Furthermore, this process of decontamination and of cleaning up is particularly advantageous due to the fact that it is based on the use of a photocatalyst that can be activated by far-infrared radiation emitted by the heating layer of the sudation device and which as such has a photocatalytic performance that is high enough even in the environment of the internal volume of the device with little or no ultraviolet light, and this without it being necessary to provide a source of energy dedicated to the activation thereof.

Preferably, said photocatalyst comprises a photocatalytic product formed from a metal and/or ceramic substrate on the surface of which is formed a layer of titanium dioxide.

Advantageously, said heating layer is able to emit infrared radiation in a range of wavelengths between 5 and 20 micrometres and more advantageously between 8 and 14 micrometres.

Advantageously, said photocatalyst housing comprises a frame of substantially elongate shape, fixed between two inside ends, along the longitudinal axis, of said cover element, in such a way as to be maintained facing and at a distance from said internal face of said heating layer covering the internal surface of said cover element.

Preferably, said frame is mounted at a distance from said internal face of said heating layer by being separated by an air gap having a thickness of at least 0.5 cm.

Preferably, the axis of said frame extends collinearly with the longitudinal axis in a plane perpendicular to said support element.

Advantageously, said frame has a cross section the shape of which follows the profile of said heating layer on said internal face of said heating layer.

Preferably, said cross section of said frame extends over a limited portion of said profile of said heating layer.

Advantageously, said frame comprises a perforated lower plateau comprising at least one reception zone intended to receive said photocatalyst and a perforated upper sheet closing said frame facing said internal face of said heating layer.

According to a particular embodiment, said photocatalyst housing furthermore integrates a fabric able to emit electromagnetic waves in the far-infrared range in substantially the same range of wavelengths as the far-infrared radiation emitted by said heating layer.

BRIEF DESCRIPTION OF THE DRAWINGS

Other particularities and advantages of the invention shall come from reading the description provided hereinafter of a particular embodiment of the invention, provided for infor

DETAILED DESCRIPTION OF THE PREFERRED EMBODIMENTS

Figure 1:
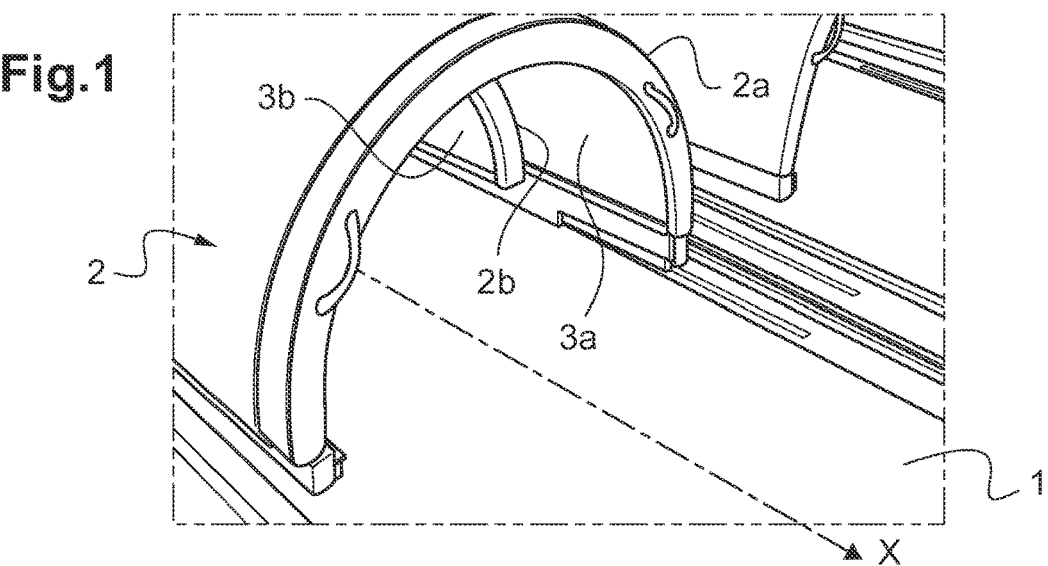
- FIG. 1 is a diagrammatic partial profile view of the sudation device by radiation with far infrared.
Figure 2:
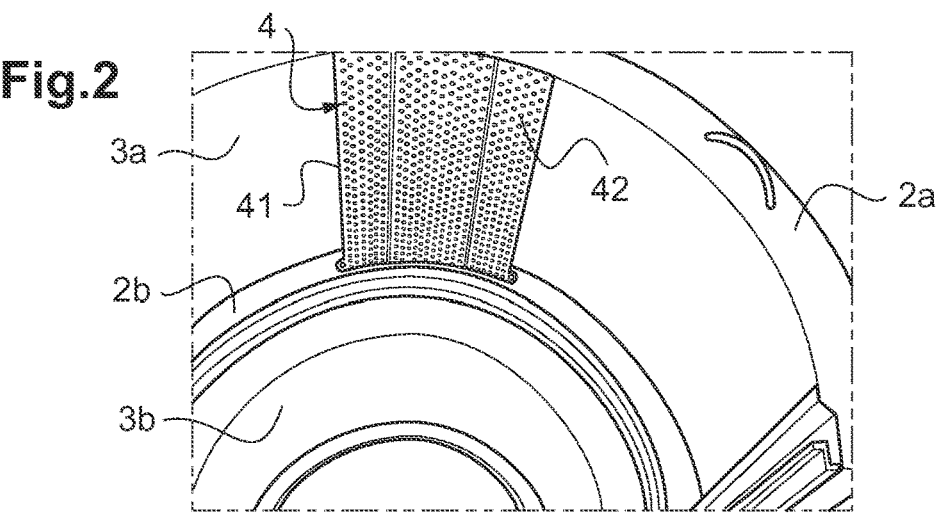
FIG. 2 is a detailed view of the inside side of the cover element of the sudation device.
Figure 3:
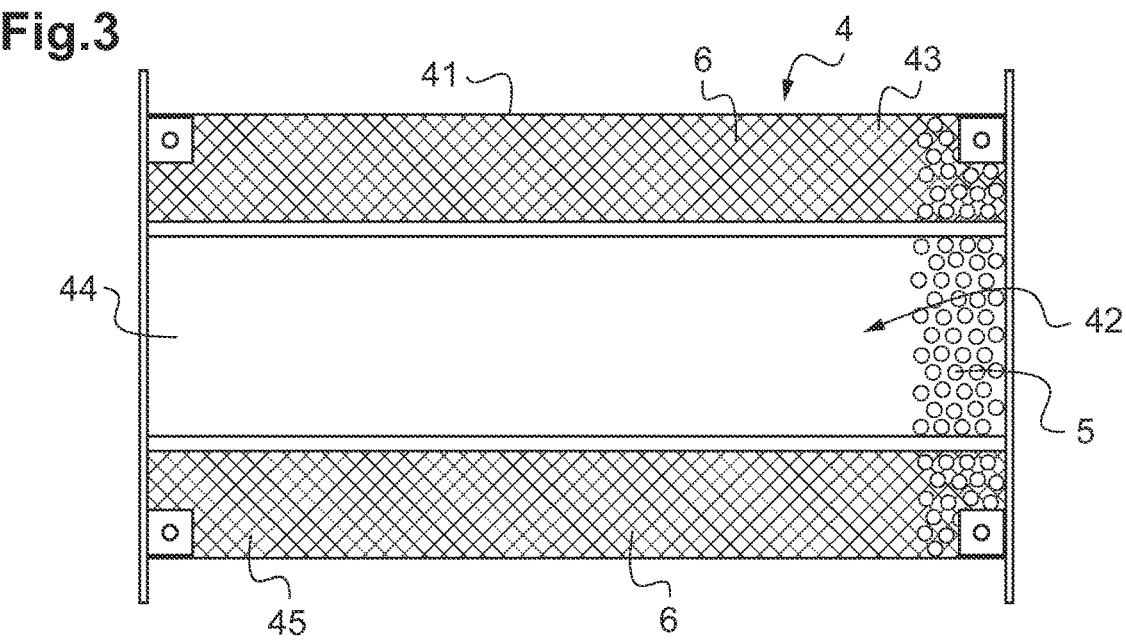
FIG. 3 is a diagrammatical top view of the photocatalyst housing shown in FIG. 2.

The infrared sudation device shown in FIG. 1 comprises a support element 1 extending along a longitudinal axis X able to receive a user in particular in the lying position. The support element 1 is surmounted by a cover element 2, of semi-cylindrical shape, which is mounted on said support element 1 along the longitudinal axis of the latter so as to delimit an internal volume extending in the longitudinal direction of the support element 1, between the upper face of the support element 1 and an internal face of the cover element 2 arranged facing the upper face of the support element 1, when the cover element 2 is mounted on the support element 1. The cover element 2 thus makes it possible to fully cover the user lying on the support element 1.

According to a preferred embodiment, the cover element 2 comprises at least one first semi-cylindrical portion 2a, called the upper semi-cylindrical portion, intended to cover the portion of the body of the user located towards his head, and a second semi-cylindrical portion 2b, referred to as lower semi-cylindrical portion, intended to cover the portion of the body of the user located opposite the head. The second semi-cylindrical portion 2b has for example a diameter less than the diameter of the first semi-cylindrical portion 2a and the first and second semi-cylindrical portions 2a and 2b are coupled together in such a way that they can slide with respect to one another along the longitudinal direction X, by means of a sliding system, for example by means of sliders arranged on lateral portions of the support element 1, parallel to the longitudinal axis X. In particular the first cylindrical portion 2a can slide along the longitudinal direction X on the second cylindrical portion 2b, in such a way as to be adjusted to the size of the user. One end, not shown, of the second semi-cylindrical portion 2b of the cover element 2 is closed off by a semicircular plate, making it possible to close at this end the internal volume wherein the user is intended to settle.

Each semi-cylindrical portion 2a, 2b is provided on its internal face, i.e. the surface located on the same side as said internal volume, of a heating layer, respectively 3a, 3b, able to emit an infrared radiation, and more particularly a far or long infrared radiation, in the internal volume located between the internal face of the heating layer (i.e. the face facing the support element) and the support element 1. The semicircular plate closing the internal volume at one end can also be provided on its internal face with such a heating layer. Each heating layer 3a, 3b is mounted on the internal face of the corresponding portion of the cover element in such a way as to substantially cover the entire internal face by hugging the profile of this internal face. Thus the profile of the heating layer makes it possible to obtain an emission of infrared radiation distributed in an optimum manner over the entire surface of the body of the user with a convergence zone of the radiation emitted located substantially along the longitudinal axis and therefore along the body of the user in lying position under the heating layer integrated into the cover element.

Each heating layer 3a, 3b has for example the form of at least one carbon plate, having a multilayer structure preferably comprising a layer with a black-carbon base, sandwiched between two glass fibre sheets. The plate is also provided with two electrodes, arranged on opposite edges of the plate, in contact with the layer with a black-carbon base and able to be supplied by means of supply means (not shown) controlled by a controller. When the layer with a black-carbon base is supplied by means of electrodes, it is heated while emitting long-infrared radiation over its entire surface. Preferably, the supply to the heating layer is controlled in such a way as to emit long infrared radiation in the range of wavelengths between 5 and 20 µm, preferably between 8 and 14 µm. Such radiation received by the body of the user has a high power of penetration into the tissues of the skin and makes it possible to cause a rise in the surface temperature of the body of the user. Such radiation causes a stimulation of the tissues of the skin and in particular a stimulation of the sweat glands, which favours the excretion of chemical products that are toxic for the human body, in particular the toxic heavy metals to which the user may have been exposed.

Provision is furthermore made, in accordance with the invention, to clean up the air in the internal volume delimited by the support element 1 and its cover element 2, by associating a photocatalyst system with the emission of long-infrared radiation in this internal volume, which can be activated by said radiation, in order to prevent a saturation of the air with chemical products excreted by the sweat of the user subjected to long-infrared radiation.

To do this, the photocatalyst system implemented comprises a photocatalyst housing 4, permeable to the infrared radiation emitted, supporting a photocatalyst 5 and being arranged in proximity to the internal face of the heating layer 3a of the first semi-cylindrical portion 2a of the cover element 2, in such a way as to allow for the activation of the photocatalyst using the energy supplied by the infrared radiation emitted by the heating layer. Provision can also be made to equip in the same way the second semi-cylindrical portion 2b of the cover element 2 with such a photocatalysis system.

According to the embodiment shown in the figures, the housing 4 comprises a frame 41, preferably made of metal, of substantially elongate shape, fixed between two inside ends, along the longitudinal axis X, of the first semi-cylindrical portion 2a of the cover element, in such a way as to be maintained facing and at a certain distance from the internal face of the heating layer 3a. The frame 41 is arranged facing the internal face of the heating layer in such a way that its axis extends preferably collinearly with the longitudinal axis X in a plane perpendicular to the support element. In other words, the frame 41 extends preferably along the apex of the cover element. The frame 41 further comprises a cross section the shape of which substantially follows the profile of the heating layer 3a on the internal face of the heating layer 3a across from which it is arranged and this cross section extends preferably over a limited portion of the profile of the heating layer, on either side of the apex. Preferably, the frame 41 is mounted at a distance from the internal face of the heating layer 3a by being separated by an air gap having a thickness of at least 0.5 cm.

The frame 41 comprises a perforated lower plateau 42, forming a grid, wherein are arranged reception zones separated by separation partitions, for example three reception zones 43, 44, 45, which extend longitudinally in the frame and of which at least the central reception zone 44 is intended to receive the photocatalyst.

This grid 42 is covered with a perforated upper sheet (not shown) closing the frame facing the internal face of the heating layer 3a. Thus the structure of the unit forming the frame is permeable to the long infrared radiation emitted by the heating layer thanks to the perforated zones and the passage of the long-infrared radiation emitted by the heating layer 3a through the perforated zones of the frame will make it possible to excite the photocatalyst 5 stored inside the reception zones of the frame 41.

In a particular embodiment, the photocatalyst housing 4 integrates a fabric able to emit electromagnetic waves in particular in the far-infrared range, in substantially the same range of wavelengths as the infrared radiation emitted by the heating layer. Thus, according to this particular embodiment, the lateral reception zones 43, 45, which extend on each side of the central reception zone 44 wherein is received the photocatalyst 5, are intended to receive a layer of fabric 6 made from fibres, in particular fibres as described in patent document EP 2072666, containing nanometric diamond and a nanometric platinum colloid, with the nanometric diamond and the platinum nanometric colloid being fixed to said fibres. Such fibres have an excellent capacity to emit far-infrared radiation. Integrating such a fabric into the photocatalyst housing 4 makes it possible to amplify the far-infrared radiation emitted in the internal volume of the device thanks to the natural emission capacity of such a radiation that this fabric has. This amplification effect is all the more notable since the action of this fabric is favoured by the heat produced by the heating layer, which heats to a temperature of about 55 to 70° C. Furthermore, the photocatalyst housing 4 forms a sort of screen in front of the heating layer 3a at the location where it is arranged, which is substantially along the apex of the cover element according to the embodiment, since the portions between the perforated zones of the frame are detrimental to the proper propagation to the internal volume of the long-infrared radiation emitted from the apex of the cover element. Thus integrating the layer of fabric 6 in the photocatalyst housing 4 makes it possible to compensate for this relative loss of far-infrared radiation emitted by the heating layer on the apex of the cover element and thus makes it possible to obtain a distribution of the emission of the infrared radiation that is relatively uniform within the internal volume, despite the presence of the photocatalyst housing 4.

The photocatalyst 5 stored in the photocatalyst housing 4, and for example in the central reception zone inside the frame 41, comprises a photocatalytic product, that has for example the shape of balls of small size, preferably of about 15 to 20 mm in diameter, coated with a photocatalyst. Each ball thus forms a photocatalyst agent and more precisely consists of a metal and/or ceramic substrate on the surface of which is formed a layer of titanium dioxide applied according to the method of manufacture described in patent EP 0980709. This technology is known as the "PIP process", PIP being an acronym for "Powder Impact Plating".

The term photocatalyst agent designates an agent able to destroy the various organic pollutants present in the air, and this via a photocatalytic reaction caused by the irradiation of the photocatalyst agent with the long-infrared rays emitted by the heating layer 3a. This chemical reaction is well known by the term photocatalysis and is advantageously here implemented for the treatment and the cleaning up of the air included in the volume of air between the cover element and the support element during a sweating session via long infrared. Thus the polluting particles in suspension in the air and coming into contact with the surfaces of the photocatalyst agents treated with the photocatalyst coating are broken down by the photocatalytic reaction.

The invention claimed is:

1. An infrared sudation device comprising:
   a support element extending along a longitudinal axis configured to receive a user in a lying position;
   a cover element of semi-cylindrical shape mounted on said support element to delimit an internal volume extending in a longitudinal direction of said support element between said support element and an internal surface of said cover element, said internal surface of said cover element being covered at least in part with a heating layer able to emit far-infrared radiation in at least one portion of said internal volume; and
   a photocatalyst housing, permeable to the infrared radiation emitted, supporting a photocatalyst and being arranged proximate an internal face of said heating layer to allow said photocatalyst to be activated using energy supplied by said infrared radiation emitted;
   wherein said photocatalyst housing comprises a frame of substantially elongate shape, fixed between two inside ends, along the longitudinal axis, of said cover element, in such a way as to be maintained facing and at a distance from said internal face of said heating layer covering the internal surface of said cover element.

2. Device according to claim 1, wherein said heating layer is able to emit infrared radiation in a range of wavelengths between 5 and 20 micrometres.

3. Device according to claim 1, wherein said frame is mounted at a distance from said internal face of said heating layer by being separated by an air gap having a thickness of at least 0.5 cm.

4. Device according to claim 1 wherein an axis of said frame extends collinearly with the longitudinal axis in a plane perpendicular to said support element.

5. Device according to claim 1, wherein said frame has a cross section with a shape following a profile of said heating layer on said internal face of said heating layer.

6. Device according to claim 5, wherein said cross section of said frame extends over a limited portion of said profile of said heating layer.

7. Device according to claim 1 wherein said frame comprises a perforated lower plateau comprising at least one reception zone receiving said photocatalyst and a perforated upper sheet closing said frame facing said internal face of said heating layer.

8. Device as claimed in claim 1, wherein said photocatalyst housing integrates a fabric able to emit electromagnetic waves in the far-infrared range in substantially a same range of wavelengths as the infrared radiation emitted by said heating layer.

9. Device according to claim 1, wherein said heating layer is able to emit infrared radiation in a range of wavelengths between 8 and 14 micrometres.

10. An infrared sudation device comprising:
    a support element extending along a longitudinal axis configured to receive a user in a lying position;
    a cover element of semi-cylindrical shape mounted on said support element to delimit an internal volume extending in a longitudinal direction of said support element between said support element and an internal surface of said cover element, said internal surface of said cover element being covered at least in part with a heating layer able to emit far-infrared radiation in at least one portion of said internal volume; and a photocatalyst housing, permeable to the infrared radiation emitted, supporting a photocatalyst and being arranged proximate an internal face of said heating layer to allow said photocatalyst to be activated using energy supplied by said infrared radiation emitted;
wherein said photocatalyst comprises a photocatalytic product formed from a metal and/or ceramic substrate on a surface of which is formed a layer of titanium dioxide.

* * * * *